(12) United States Patent
Stranska et al.

(10) Patent No.: US 11,771,648 B2
(45) Date of Patent: Oct. 3, 2023

(54) CARRIER FOR OROMUCOSAL ADMINISTRATION OF PHYSIOLOGICALLY ACTIVE SUBSTANCES

(71) Applicant: INSTAR TECHNOLOGIES A.S., Liberec III-Jerab (CZ)

(72) Inventors: Denisa Stranska, Liberec (CZ); Adela Klabanova, Jablonec nad Nisou (CZ); Pavel Dolezal, Hradec Kralove (CZ); Petr Vrbata, Studenka (CZ); Pavel Berka, Opava (CZ); Marie Musilova, Hradec Kralove (CZ)

(73) Assignee: INSTAR TECHNOLOGIES A.S., Liberec III Jerab (CZ)

( * ) Notice: Subject to any disclaimer, the term of this patent is extended or adjusted under 35 U.S.C. 154(b) by 632 days.

(21) Appl. No.: 16/867,470

(22) Filed: May 5, 2020

(65) Prior Publication Data
US 2020/0261353 A1    Aug. 20, 2020

Related U.S. Application Data

(60) Division of application No. 15/712,631, filed on Sep. 22, 2017, now abandoned, which is a continuation of application No. 13/979,039, filed as application No. PCT/CZ2011/000116 on Dec. 12, 2011, now Pat. No. 9,789,060.

(30) Foreign Application Priority Data

Jan. 17, 2011    (CZ) .................................. CZ2011-24

(51) Int. Cl.
*A61K 9/00*    (2006.01)
*A61K 9/70*    (2006.01)

(52) U.S. Cl.
CPC ................ *A61K 9/006* (2013.01); *A61K 9/70* (2013.01)

(58) Field of Classification Search
CPC ...... A61K 9/006; A61K 9/70; A61K 2300/00; A61K 31/4196; A61K 31/4439; A61K 45/06; A61P 11/00; A61P 19/02; A61P 25/06; A61P 29/00; A61P 3/10; A61P 31/00; A61P 35/00; A61P 43/00; A61P 7/02; A61P 9/00
See application file for complete search history.

(56) References Cited

U.S. PATENT DOCUMENTS

| 4,666,441 | A | * | 5/1987 | Andriola | A61F 13/0259 604/304 |
| 4,889,720 | A | * | 12/1989 | Konishi | A61K 9/006 424/435 |
| 6,319,510 | B1 | | 11/2001 | Yates | |
| 8,231,822 | B2 | | 7/2012 | Petras et al. | |
| 10,052,291 | B2 | | 8/2018 | Hansen et al. | |
| 2003/0017208 | A1 | * | 1/2003 | Ignatious | D01D 1/02 424/486 |
| 2007/0207179 | A1 | * | 9/2007 | Andersen | A61B 17/12172 523/105 |
| 2008/0284050 | A1 | | 11/2008 | Pietro et al. | |
| 2008/0307766 | A1 | | 12/2008 | Petras et al. | |
| 2010/0166854 | A1 | * | 7/2010 | Michniak-Kohn | A61L 27/58 424/456 |
| 2010/0194000 | A1 | * | 8/2010 | Petras | D01D 5/0069 264/484 |
| 2012/0148493 | A1 | | 6/2012 | Schmehl et al. | |

FOREIGN PATENT DOCUMENTS

| CN | 101327182 A | 12/2008 | |
| CN | 101336885 A | 1/2009 | |
| CN | 102614106 A | 8/2012 | |
| EP | 589692 A1 | 5/2013 | |
| JP | H05124476 A | 5/1993 | |
| KR | 100806412 B1 | 2/2008 | |
| KR | 20100092545 A | 8/2010 | |
| KR | 20120005989 A | 1/2012 | |
| WO | 2009022761 A1 | 2/2009 | |
| WO | 2009133059 A2 | 11/2009 | |
| WO | WO2012/097763 A2 * | 7/2012 | ............... A61K 9/00 |

OTHER PUBLICATIONS

Yarin, et al, "Upward needleless electrospinning of multiple nanofibers," Polymer, 2004, vol. 45, No. 9, pp. 2977-2980.
Vrbata Petr et al., "Electrospun drug loaded membranes for sublingual administration of sumatriptan and naproxen", International Journal of Pharmaceuticals, vol. 457, No. 1, Feb. 15, 2008, pp. 168-176.
Fathi-Azarbayjani et al., "Single and Multi-Layered Nanofibers for Rapid and Controlled Drug Delivery", Chem. Pharm. Bull., Feb. 2010, 58(2), 143-146.
Deng-Guang Yu et al., "Multicomponent Amorphous Nanofibers Electrospun from Hot Aqueous Solutions of a Poorly Soluble Drug", Parm. Res., 2010, vol. 27, pp. 2466-2477.
Nagy, ZS. K. et al, "Electrospun water soluble polymer mat for ultrafast release of Donepezil Hcl", Express Polymer Letters, vol. 4, No. 12, Nov. 5, 2010, pp. 763-772.
Munzarova, M., "Nanofibers in medical applications", Dec. 22, 2010, XP55033243, Retrieved from the internet: URL: Http://svu2000.org/conferences/tabor2010/D1-6-munzarova.pdf [retrieved on Jul. 19, 2012].

(Continued)

*Primary Examiner* — Audrea B Coniglio
(74) *Attorney, Agent, or Firm* — Rimon PC

(57) ABSTRACT

The invention relates to a carrier for oromucosal, especially sublingual administration of physiologically active substances, especially of medicinal drugs, which consists of at least one elastic layer (1) of polymer nanofibres workable according to the shape of the selected wall of mouth cavity to which it should be applied and in this elastic layer (1) of polymer nanofibres a drug and/or other physiologically active substance are deposited in a releasable manner.

14 Claims, 4 Drawing Sheets

(56) References Cited

OTHER PUBLICATIONS

International Search Report dated Jul. 26, 2012 from corresponding International Patent Application No. PCT/CZ2011/000116.
Karthikeyan, D. et al., "Deveopment of Fast Dissolving Oral Film Containing of Rizatriptan Benzoate as an Antimigraine Medication Corresponding author", Indo American Journal of Pharmaceutical Research Indo American Journal of Pharm Research, Jan. 1, 2013, Retrieved from the Internet: URL:http//www.ejmanager.com/mnstemps/36/36-1395220993.pdf [retrieved on Mar. 6, 2017] the whole document.

* cited by examiner

CARRIER FOR OROMUCOSAL ADMINISTRATION OF PHYSIOLOGICALLY ACTIVE SUBSTANCES

CROSS REFERENCE TO RELATED APPLICATIONS

This application is a Divisional Application of U.S. patent application Ser. No. 15/712,631, filed Sep. 22, 2017, currently pending, which is a Continuation Application of U.S. patent application Ser. No. 13/979,039, filed Aug. 16, 2013, now issued, which was a 35 U.S.C. § 371 National Phase conversion of PCT/CZ2011/000116, filed Dec. 12, 2011, which claims benefit of Czech Republic Application No. PV 2011-24, filed Jan. 17, 2011, the disclosure of each of which is incorporated herein by reference. The PCT International Application was published in the English language.

TECHNICAL FIELD

The invention relates to a carrier for oromucosal, especially sublingual administration of physiologically active substances, especially medicinal drugs.

THE STATE OF THE ART

At present, the therapy of many diseases is connected with administration of medicinal drugs. The most common form of drug administration is oral administration by mouth, linked with swallowing of tablets or capsules, after which the drug passes through the gastrointestinal tract (GIT), where the drug is gradually released upon, especially in the stomach and in the intestine. Upon systemic administration (in contrast to administration intended only for local action in the GIT) the drug is, mostly only a certain portion of it, absorbed from the GIT into the blood or lymphatic system and transported by it primarily into the liver. During this whole route the drug is being transformed in a certain manner. In many cases, its efficiency is thus reduced and with regard to this, the dose necessary to ensure the desired action has to be increased. This may cause an increase in undesirable side effects of such a drug. There exists an important group of drugs and/or physiologically active substances of which, for example, insulin can be mentioned. They are, when passing through the gastrointestinal tract and/or when being absorbed by its wall, especially by the stomach and intestinal wall, or during the subsequent first passage through the liver, completely or in a substantial extent inactivated or split into inactive metabolites. Therefore, there are other routes, for example parenteral routes of administration of such drugs (excluding the GIT). They include, for example, absorption from a sublingual tablet through the mouth cavity mucosa, absorption from patches or plasters into the skin, or intravenous administration by injection or infusion.

For example, insulin is administered in a subcutaneous way, either using a hypodermic needle, insulin pens or pumps. Sublingual administration of this substance seems to be impossible at present/as it is inactivated in contact with saliva and its absorption from badly definable absorption surface is in principle very variable.

Another group of physiologically active substances, where sublingual administration seems to be reasonable, is represented by well absorbable substances with a rapid onset of action. These are the drugs belonging to the therapeutic groups treating, e.g. migraine pain, fast approaching pain attacks in cancer therapy, anxiety and panic states.

Other therapeutically interesting groups of substances, for which the sublingual administration seems to be possible and advantageous, are represented by the drugs for mitigation and therapy of Parkinson's disease, Alzheimer's disease, or schizophrenia.

The general advantages of sublingual administration of drugs include fast permeation of physiologically active substance through a relatively thin and permeable biological membrane, which does not exert its own enzymatic activity and whose vasculature does not lead the absorbed substances directly to the liver. Therefore the sublingual administration seems to be advantageous for administration of drugs which have to be delivered into the blood circulation very quickly (drugs with rapid onset of action), which are not resistant to pH and to enzymes of GIT, and which undergo a high first-pass metabolism.

The problem of the present sublingual administration of drugs is especially due to the fact that the surface of the sublingual mucosa in the mouth cavity is under physiological conditions constantly washed by saliva which is continuously swallowed. Also, activity of the tongue prevents a longer contact of the drug with the sublingual mucosa. The sublingual tablets being used are thus formulated as very rapidly soluble and serve for administration of the physiologically active substances which are capable to permeate through the sublingual membrane into the vascular system very quickly before they are either deteriorated by saliva and other substances present in the mouth cavity, or possibly swallowed with them.

From the professional literature are known non-fibrous membrane carriers (e.g. strips, films) and attempts to create drug carriers containing a nanofibrous layer or layers produced by the use of electrospinning of polymer solutions or melts from a needle or a nozzle. A drug is applied onto such a nanofibrous layer in the form of a liquid which is, e.g., poured and dried, or a drug is layered in a solid state by extrusion. A disadvantage of such a way of creating non-fibrous membranes, as well as the nanofibrous layers, is their low air permeability and high fragility, which does not permit any realistic administration of them into the sublingual space. During attempts to enable such administration, various platisticizers were used without significant positive results. Another disadvantage consists in a difficult pre-defining of the quantity of a drug which sticks, with the use of these technologies of production, to the nanofibrous layer, and problematic reproducibility of the final products resulting from it, because the nanofibrous layer is produced in small sizes and its dipping into a solution of active ingredients or the administration of active substances using extrusion does not guarantee a repeatedly stable and releasable quantity of the applied substance.

The goal of the invention is to create a carrier suitable for sublingual administration of physiologically active substances, in particular drugs, which would resolve the disadvantages of the state of the art and would also enable further oromucosal administrations.

PRINCIPLE OF THE INVENTION

The goal of the invention has been achieved by a carrier for oromucosal, especially for sublingual administration of physiologically active substances, in particularly medicinal drugs. The essence is of the invention is that the carrier comprises at least one elastic layer of polymer nanofibres being shapeable according to the shape of a selected wall of the mouth cavity to which it should be applied, and in this elastic layer of polymer nanofibres it contains a releasable drug and/or other physiologically active substance. The elasticity and shapeability of the layer of polymer nanofibres in the given context as a reservoir of the physiologically active substances, especially drugs, enables a perfect contact of the layer with the selected wall of the mouth cavity, thus enabling good penetration of the drug and/or other physiologically active substance into this wall, or a possible transfer through it into the vascular system and into the human or animal organisms. Workability and elasticity of the layer of nanofibres are achieved due to the production of a layer of nanofibres through needleless electrostatic spinning, in which simultaneously with a polymer also a drug and/or other physiologically active substance are being subjected to spinning, which are then deposited in a releasable manner in the layer of nanofibres, and which can extend to the surface of the nanofibres or can be on the surface of the nanofibres chemically or physically bound. It is advantageous for an easy fixation on the selected wall of the mouth cavity if the layer of polymer nanofibres is on one of its sides provided with adhesive means, the adhesive means being preferably a layer of polymer nanofibres containing drugs and/or other physiologically active substances, or these means are represented by an elastic adhesive layer applied to the edges of the layer of polymer nanofibres.

According to further embodiment of the invention, the layer of polymer nanofibres containing a releasably deposited drug and/or other physiologically active substance is covered from all sides with an elastic and shapeable oromucosally non-adhesive covering layer. This embodiment has been designed to be inserted into the mouth cavity without fixation to some of the walls of the mouth cavity.

In one of its possible embodiments, the covering layer is permeable for saliva and for substances contained in the mouth cavity and if a drug and/or other physiologically active substance is releasably deposited in the layer of polymer nanofibres and is soluble by saliva and/or by substances contained in the mouth cavity, it is leached from the layer of nanofibres by saliva into the mouth cavity, where it acts at least for a period of its release.

For some administrations of the carrier it is at the same time advantageous if the covering layer is insoluble by saliva and by substances contained in the mouth: cavity, while it is permeable for a drug and/or other physiologically active substance releasably deposited in the layer of polymer nanofibres, and the drug and/or other physiologically active substance is released from the layer of nanofibres in passive contact of the covering layer with the wall of the mouth cavity and/or by pressure, e.g. during chewing. At this embodiment the user must be in advance informed about for how long to hold the carrier in his mouth so that the whole necessary dose of the drug and/or other physiologically active substance is released. For other administrations of the carrier, the covering layer as well as the layer of polymer nanofibres are soluble by saliva and/or substances contained in the mouth cavity, while the period of time of their dissolution is longer than the time time of the release of the drug and/or other physiologically active substance from the layer of nanofibres, so that after the release of the drug and/or other physiologically active substance from the layer of nanofibres the layer of nanofibres as well as the covering layer in the mouth starts to dissolve, which is the signal for the user that the process is finished and the rest of the carrier can be removed or swallowed.

Another important group of carriers according to the invention are the carriers in which the layer of polymer nanofibres from the side which should be directed into the free space of the mouth cavity at the administration of the carrier is covered by an elastic and workable oromucosally non-adhesive covering layer, while the other side of the layer of polymer nanofibres remains free and by means of it the carrier can be fixed on the selected wall of the mouth cavity as described above.

A complete protection of the elastic layer of polymer nanofibres, in which a drug and/or other physiologically active substance is releasably deposited, is achieved by a carrier whose principle consists in that the layer of polymer nanofibres is covered from the side which should be directed into the free space of the mouth cavity during the administration of the carrier with an elastic and workable oromucosally non-adhesive covering layer, and from the side designated to be in contact with some of the walls of the mouth cavity during administration covered with an elastic and workable protective layer, which is permeable for the drug and/or other physiologically active substances releasably deposited in the layer of polymer nanofibres, by which it enables in contact with the respective wall of the mouth cavity penetration of the drug and/or other physiologically active substance into this wall, as well as a possible transfer through it into the vascular system and into the human or animal organisms, while the covering layer and the protective layer are connected on their edges.

To enable possible fixation of such a carrier to the selected wall of the mouth cavity, the protective layer is provided with at least one adhesive means, which in the preferred embodiment consists of an adhesive layer applied to the edges of the protective layer. As a result of this, the surface of the protective layer which is in contact with the selected wall of the mouth cavity is reduced and the portion of the drug and/or other physiologically active substance positioned behind the adhesive layer is not released from the layer of polymer nanofibres, or is being released slowly. Therefore this adhesive means can also comprise a portion of the drug and/or other physiologically active substance.

In the case required by the use of the above mentioned carrier, it can be produced in such a way that the oromucosally non-adhesive covering layer and/or the protective layer overlap on the edges the layer of polymer nanofibres, in which the drug and/or other physiologically active substance are releasably deposited and create a fixation rim around it, surrounding at least partially its perimeter, while on the side designed for contact with some of the walls of the mouth cavity is the fixation rim provided with an elastic adhesive layer, so that the adhesive layer does not reduce the effective surface of the layer of polymer nanofibres or the effective surface of the protective layer corresponding to this surface.

In an advantageous embodiment the fixation rim is formed of adhesive material, the whole protective layer designed for contact with some of the walls of the mouth cavity can be made of the adhesive material.

In an advantageous embodiment the protective layer can be made of a layer of nanofibres.

For some administrations of the carrier according to the invention, it is advantageous if the layer or layers of nanofibres containing the drug and/or other physiologically active substance and/or the covering layer and/or the protective layer is made of a material biodegradable by the action of the medium in the mouth cavity, the time period of biodegradation being longer than the time period of the release of the drug and/or other physiologically active substance. After releasing the drug and/or other physiologically active substance from the layer of polymer nanofibres, there occurs biodegradation, which is the signal for the user that the process of releasing has been accomplished and the rest of the carrier can be removed or swallowed. In one of the advantageous embodiments of the carrier according to the invention, the drug and/or other physiologically active substance are a component of nanofibres, which ensures elasticity and workability of the carrier according to the need to achieve a perfect transfer through the wall of the mouth cavity, for example through the sublingual mucosa, and makes it possible to deposit into the carrier only a very small quantity of the drug and/or other physiologically active substance, which is nevertheless sufficient for the required medical purpose. This decreases the toxic loading of the organism by the drug and in the highly priced drugs also the costs of therapy.

For broader use of the carrier it is advantageous if it contains at least two elastic and workable layers of polymer nanofibres and in each of them a drug and/or other physiologically active substance are deposited in a releasable manner.

At the same time in each layer of polymer nanofibres there a different drug and/or other physiologically active substance can be deposited and the drugs and/or other physiologically active substances deposited in individual layers can have different rates of release.

For the drugs and/or other physiologically active substances which cannot be deposited into the layer of nanofibres during spinning, e.g. insulin, it is advantageous if these substances are impregnated into the layer of polymer nanofibres placed between the covering and protective layers. In this embodiment the drug and/or other physiologically active substance are carried by the layer of polymer nanofibres, but they are not bound in it.

EXAMPLES OF EMBODIMENT

Figure 1:
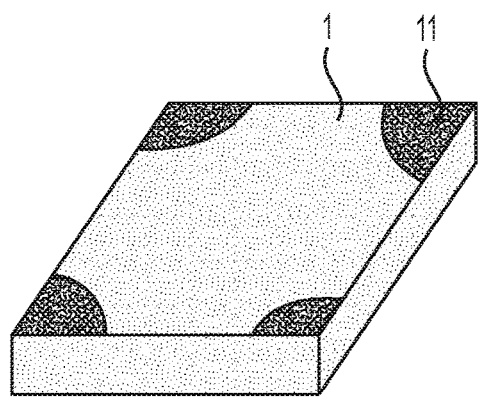
FIG. 1 represents a view of the carrier according to the invention formed only of a layer of nanofibers.

The carrier for oromucosal, in particular sublingual administration of physiologically active substances, especially drugs, comprises a nanofibrous layer in which a drug and/or other physiologically active substance are releasably deposited, the drug and/or other physiologically active substance are either deposited directly in nanofibres, of which it is a component and to whose surface it may rise, or they are situated in the space between the nanofibres and get also stuck on their surface. The basic methods of how to implant the drugs into the nanofibrous layer are coating, sinking or encapsulation by coaxial and emulsion electrospinning.

Into the space between the nanofibres of the layer of polymer nanofibres a drug and/or other physiologically active substance can be deposited by applying the drugs and/or other physiologically active substances on the produced nanofibrous layer in the form of a solution or other dispersion, which contains the drug and/or other physiologically active substance.

Onto a produced nanofibrous layer the drug and/or other physiologically active substance can be applied by wetting the layer in a solution, or by spreading the dispersion, or by spraying. In the above-mentioned cases the basic problem is the unevenness of the quantity of the applied drug and/or other physiologically active substance on the surface of the layer of nanofibres, and further disadvantages mentioned in the state of the art section.

The evenness of distribution of a drug and/or other physiologically active substance on the entire surface of the layer of polymer nanofibres can be achieved by a process of sinking, i.e. dosing of the drug and/or other physiologically active substance into a solution or a melt from which the nanofibrous layer is produced. The drug or other physiologically active substance are carried out from the solution or melt together with the polymer and remain a component of the nanofibre or emerge to its surface, to which they remain fixed. The evenness of distribution of the drug and/or other physiologically active substance thus depends on the evenness in the distribution of polymer fibres in the layer and on the evenness in the distribution of the diameters of nanofibres in the layer. The required evenness can be achieved through a long-term stable spinning process, which is at present represented by needleless electrostatic spinning of a polymer matrix in an electrical field created between the spinning electrode and the collecting electrode, e.g. according to the European Patent EP 1673493, or according to the European Patent EP 2059630, or according to the European Patent Registration Form EP 2173930.

The layer of polymer nanofibres containing a drug and/or other physiologically active substances prepared in this manner is subsequently divided into portions of specified size, weight and thus also the content of a drug and/or other physiologically active substance. These portions of the layer of polymer nanofibres can become the carrier for oromucosal, especially for sublingual administration of physiologically active substances according to the invention independently, or they are a component of the carrier, which is at least from one side covered by the protective layer. Due to the fact that the portions are made of a textile layer of polymer nanofibres, they are elastic and workable according to the shape of a given wall of the mouth cavity to which they should be applied.

In the embodiment according to FIG. 1 the carrier according to the invention is made only of layer 1 of polymer nanofibres in which there is a drug and/or other physiologically active substance deposited releasably in nanofibres or on their surface. The layer of polymer nanofibres represents a fibrous textile formation, whose basic properties are elasticity and workability, and these properties are not affected in any manner by the presence of the drug and/or other physiologically active substance. Elasticity and workability of the layer of polymer nanofibres enable a perfect contact of the layer with the given wall of the mouth cavity. It makes possible good penetration of a drug and/or other physiologically active substance into the pertinent wall of the mouth cavity a, possible transfer through this wall, e.g. through the sublingual mucosa, into the vascular system and into the human or animal organisms. Elasticity and workability of the layer of nanofibres results from the production of the nanofibrous layer using needleless electrostatic spinning, during which also the drug and/or other physiologically active substance are subjected to spinning simultaneously with the polymer, which is thus releasably deposited into the layer of nanofibres and they can also extend to the surface of nanofibres or can be bound on the surface of nanofibres either chemically or physically. The carrier can be used for oromucosal or for sublingual administration in the cases when it either does not matter, or when it requires leaching of the drug and/or other physiologically active substance by saliva, and/or by the substances contained in the mouth cavity, or in the cases when it contains drugs and/or other physiologically active substances, which are insoluble or very slowly soluble by saliva and/or other substances contained in the mouth cavity and at the same time they are able to pass through the sublingual mucosa or through another wall of the mouth cavity to which they may be applied. To secure the position on the respective Wall of the mouth cavity, layer 1 of nanofibres is provided on the side designed for contact with given wall of the mouth cavity by at least one adhesive means, for example by elastic adhesive layer 11, designed to fix the carrier oh the given wall of the mouth cavity. The adhesive layer 11 is in the represented embodiment in the corners of the portion made of a nanofibrous layer forming the carrier, or it can be made along the edges of layer 1 of nanofibres. The adhesive means can consist of the proper layer 1 of polymer nanofibres produced from a polymer suitable for this purpose, e.g. a polysaccharide.

Figure 2:
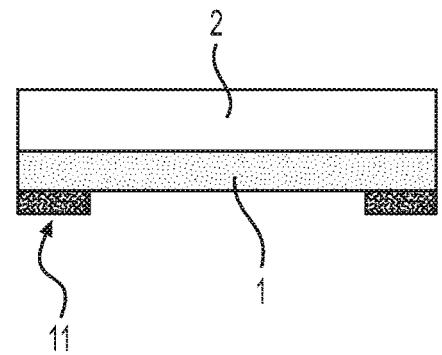
FIG. 2 shows the section of the carrier made of a layer of nanofibres and a covering layer placed on one side of the nanofibrous layer.

In the embodiment represented in FIG. 2, layer 1 of polymer nanofibres containing a drug and/or other physiologically active substances covered from one side with oromucosally non-adhesive covering layer 2, while the free side of layer 1 of nanofibres is designated for contact with the sublingual mucosa or some other wall of the mouth cavity and enables penetration of the drug and/or other physiologically active substance into this wall, and possibly through it into the vascular system and into the human or animal organisms. The covering layer 2 is usually impermeable for saliva and substances contained in the mouth cavity and prevents leaching of physiologically active substances from the carrier into the mouth cavity. That means that nearly all drugs and/or other physiologically active substances penetrate through the sublingual mucosa into the vascular system and into the human or animal organisms. That is why it is sufficient when in the portion of the layer of nanofibres which is a component of the carrier only the required (necessary) quantity of a drug and/or other physiologically active substance are contained, which is sufficient to achieve the desired medical or physiological effect, without necessity to take into account the pertinent limits of bioavailability in other parts of the GIT.

Figure 2A:
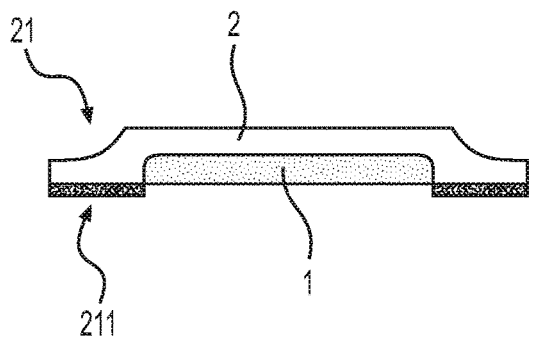
FIG. 2A depicts a section of the carrier according to FIG. 2 with a fixation rim around the perimeter of the carrier.

In the production of layer of polymer nanofibres, covering layer 2 forms the substrate layer on which nanofibres produced with the use of electrostatic spinning are deposited into the required layer. To create the portions containing layer 1 of nanofibres and covering layer 2 and forming the carrier according to the invention, it is then sufficient to cut the produced layer of nanofibres together with the substrate layer in some of the routine manners, e.g. by means of a rotating knife. To secure the position on the respective wall of the mouth cavity, layer of nanofibres is provided on the side designated for contact with the intended wall of the mouth cavity with adhesive layer 11. designed to fix the carrier to the specified wall of the mouth cavity. Adhesive layer 11 is created on the edges of the portion of nanofibrous layer 1. In the advantageous embodiment of FIG. 2A, covering layer 2 overlaps layer 1 of nanofibres containing the drug and/or other physiologically active substances and creates rim 21 around this layer. The adhesive means are deposited on the overlapping rim 21. Adhesive means are preferably formed of adhesive layer 211, or the whole rim 21 can be made of an adhesive material. In the not represented embodiment, the whole layer of polymer nanofibres is produced from an adhesive material, in which the drug and/or other physiologically active substance are deposited. Similarly, covering layer 2 can be made of an elastic and flexible layer of polymer nanofibres, which may exert adhesive properties.

In another not represented embodiment, covering layer 2 is permeable for saliva and for substances contained in the mouth cavity, and the drug and/or other physiologically active substance releasably deposited in the layer of polymer nanofibres are soluble by saliva and/or by substances contained in the mouth cavity. Once the carrier is inserted into the mouth cavity, drug and/or other physiologically active substance are leached by the saliva from the layer of nanofibres into the mouth cavity, in which it acts during its presence. This embodiment of the carrier is suitable especially for drugs and/or other physiologically active substances, for which it is necessary to remain in the mouth cavity for a certain period to show their activity. Such substances can be e.g. antimicrobial agents, anti-inflammatory agents, analgetic agents designated to relieve pain including local anaesthesia, means for systematic hormonal therapy, means to influence immune system, agents for administration of enzymes, diagnostic agents, etc.

Covering layer 2 is according to one embodiment insoluble by saliva or by other substances contained in the mouth cavity; nevertheless it is permeable for the drug and/or other physiologically active substances which are releasably deposited in the layer of polymer nanofibres. The drug and/or other physiologically active substance is released from the layer of nanofibres in passive contact of the covering layer with the wall of the mouth cavity and/or by pressure, e.g. during chewing.

In another embodiment of the carrier, covering layer 2 as well as layer 1 of polymer nanofibres are soluble by saliva and/or by substances contained in the mouth cavity. The period of time of the dissolution of covering layer 2 as well as of layer 1 of nanofibres is longer than the time period of the release of the drug and/or another physiologically active substance from layer 1 of nanofibres, so that after the release of the drug and/or another physiologically active substance from layer 1 of nanofibres, the layer of nanofibres as well as the covering layer 2 start to dissolve in the mouth, which is the signal for the user that the process of the release of the drug and/or another physiologically active substance is accomplished, and the rest of the carrier can be removed from the mouth or can be swallowed.

Another important group of carriers according to the invention are the carriers in which the layer of polymer nanofibres is covered from the side which should be directed into a free space of the mouth cavity during administration of the carrier by an elastic and workable oromucosally non-adhesive covering layer 2, while the other side of layer 1 of polymer nanofibres remains free, and by means of it the carrier can be fixed on the selected wall of the mouth cavity as described above. Such a carrier represents one of the basic embodiments of the carrier according to the invention.

Figure 3:
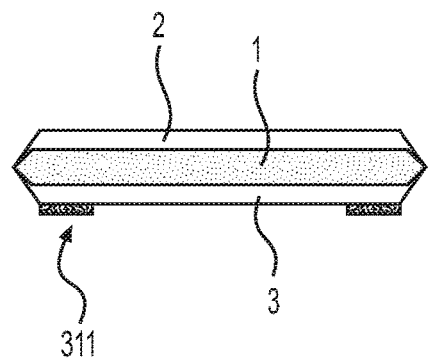
FIG. 3 depicts a section of the carrier comprising a layer of nanofibres enclosed between the covering and protective layers from all sides.

FIG. 3 shows another variant of the carrier according to the invention. In this embodiment layer 1 of polymer nanofibres containing a drug and/or other physiologically active substances is covered from the side which should be directed to a free space of the mouth cavity during administration of the carrier by the elastic and workable oromucosally non-adhesive covering layer 2, possibly adhesive, and from the other side by the protective layer 3, preferably adhesive, designated for contact with the respective wall of the mouth cavity, and the covering layer 2 as well as the protective layer 3 are joined on edges, so that the layer 1 of nanofibres is enclosed between them from all sides.

In the production of layer 1 of polymer nanofibres, e.g. covering layer 2 forms the substrate layer, on which the nanofibres produced by electrostatic spinning are deposited into the required layer 1. In the further step, to the layer 1 of nanofibres the protective layer 3 is applied, preferably an adhesive one, which can be made of another layer of nanofibres permeable for the drug and/or other physiologically active substances deposited in the nanofibres of the basic layer of nanofibres. The protective layer 3 can be also made of another suitable, adequately adhesive textile permeable for the drug and/or other physiologically active substances deposited in nanofibres of the basic layer of nanofibres. In this case the inner protective layer 3 is deposited on the surface of the layer 2 of nanofibres outside the spinning space. To create the portions 1 composed of the layer 1 of polymer nanofibres, the covering layer 2 and the protective layer 3 and forming the carrier according to the invention, it is then sufficient to cut the produced layer of nanofibres together with the covering layer 2 and the protective layer 3 in some of the routine manners, e.g. by means of a fusing rotating knife, in which by the action of heat and pressure during cutting the edges of cut-out portions join together. Cutting can be realized also by means of ultrasound or a laser.

A common technological arrangement for an expert is the variant in which the substrate textile, on which the layer of polymer nanofibres is deposited during production, is made of protective layer 3 and on the layer 1 of nanofibres the covering layer 2 is deposited.

To secure the position on the respective wall of the mouth cavity, on the side serving for contact with the pertinent wall of the mouth cavity, the inner protective layer 3 is provided with an adhesive means, e.g. adhesive layer 31, designated to fix the carrier on the specified wall of the mouth cavity. The adhesive layer is produced on the edges of the layer 1 of nanofibres.

In the basic embodiment the carrier in the embodiment according to FIG. 3 serves to release drugs and/or other physiologically active substances deposited in nanofibres of the layer 1 of polymer nanofibres through the specified wall of the mouth cavity, usually through the sublingual mucosa, to which it was applied by its inner protective layer 3. The inner protective adhesive layer 3 is permeable for drugs and/or other physiologically active substances and all drugs and/or other physiologically active substances penetrate the inner protective layer 3 and the sublingual mucosa into the vascular system and into the human and animal organisms in a 5000× magnification, while the external covering layer 2 is impermeable for saliva and other substances in the mouth cavity and during the whole period of releasing it prevents leaching of the drug and/or other physiologically active substance from the carrier into the mouth cavity.

In another embodiment, covering layer 2 of the carrier is permeable for saliva and for substances contained in the mouth cavity, and the drug and/or other physiologically active substances deposited releasably in nanofibrous layer are at least partially soluble by saliva and/or substances contained in the mouth cavity, or at least some of them are soluble. The inner protective layer 3 is at this embodiment provided with at least one adhesive means, e.g. by peripheral adhesive layer 31, by means of which the carrier may be attached to the specified wall of the mouth cavity. In the case when in the inner space of carrier at least two layers A of nanofibres are used, a different drug and/or another physiologically active substance can be deposited in each of them.

To secure perfect fixation of the carrier in the mouth cavity, the covering layer 2 as well as the protective layer 3 overlap the edges of the portion of layer 1 of polymer nanofibres, in which the drug and/or other physiologically active substance are releasably deposited, and form fixation rims 21 or 31 around it. On the side designated for contact with some of the walls of the mouth cavity, fixation rims 21, 31 are provided with flexible adhesive layers 211, 311. In the advantageous embodiment the fixation fell 21, 31. is created from an adhesive material, for example from polysaccharide.

Figure 4:
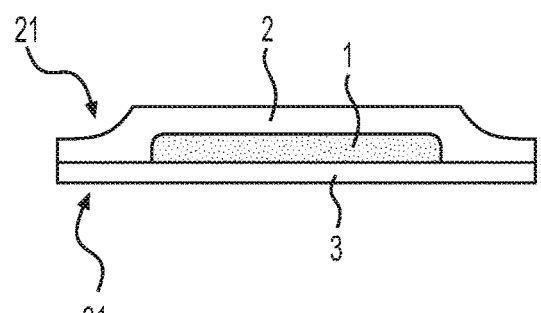
FIG. 4 depicts a section of the carrier according to FIG. 3 with a fixation rim made of a protective layer with adhesive properties.

In the embodiment according to FIG. 4, the adhesive material, e.g. a polysaccharide, forms the whole protective layer 3, from which also fixation rim 31 is created, and at the same time for securing good permeability of the drug and/or other physiologically active substance which is being released from layer 1 of polymer nanofibres, protective layer 3 is made of a layer of nanofibres.

In another example of the embodiment, layer 1 or layers of polymer nanofibres containing a drug and/or other physiologically active substance and/or the covering layer 2 and/or protective layer 3 are made of a material biodegradable by the action of the medium in the mouth cavity, the period of time of biodegradation being longer than the time period of releasing the drug and/or other physiologically active substance. After the drug and/or other physiologically active substance is released from the layer of polymer nanofibres, biodegradation of the carrier takes place, which is the signal for the user that process of the release of the drug and/or other physiologically active substance is accomplished and the rest of the carrier can be removed or swallowed.

In another advantageous embodiment which further extends the sphere of the administration of the carrier according to the invention, the carrier consists of at least two elastic and workable layers 1 of polymer nanofibres, and in each of them a drug and/or other physiologically active substance are releasably deposited. In each, layer 1 of polymer nanofibres a different drug and/or other physiologically active substance is deposited in a releasable manner. They may have identical or different releasing rates from respective layers 1 of polymer nanofibres.

For drugs and/or other physiologically active substances which cannot be incorporated into the layer of nanofibres during spinning, e.g. insulin, these substances are impregnated into the layer of polymer nanofibres arranged between the covering layer and the protective layer. In this embodiment the drug and/or other physiologically active substance are carried by the layer of polymer nanofibres, nevertheless they are not bound in it.

Below are shown model examples for the production of textiles with nanofibrous layers, which are elastic and workable and contain a drug and/or other physiologically active substances. These examples are shown as the model ones and are not intended to limit the invention to the substances mentioned in the examples, whether they; are polymers, solvents, physiologically active substances or the concrete methods of production, etc.

EXAMPLE 1

A Biodegradable Layer of Nanofibres with Caffeine Covered with a Nonbiodegradable Layer Polyurethane (PUR) was selected to serve as a non-biodegradable layer due to its widely spread administration in medicine, and polycaprolactone (PCL) was tested as a biodegradable layer. Polycaprolactone was subject to spinning as a 12% solution from AA:FA 2:1, with an addition of caffeine (5% by weight for polymer), in 13% PUR in DMF:toluene 2:1 still prior to spinning its conductivity was increased by means of tetraethylammoniumbromide (TEAB) to 30 μS.

| PCL with caffeine on a 0.5 m line | | |
|---|---|---|
| electrodes | spinning (SE) | 6-wire |
| | collecting (CE) | cylinder |
| | distance (mm) | 180 |
| | SE length (mm) | 250 |
| | CE length(mm) | 500 |
| | speed SE/min | 5 |
| voltage | SE (kV) | 60 |
| | CE (kV) | −5 |
| PUR on a 0.5 m line | | |
| electrodes | spinning (SE) | 6-wire |
| | collecting (CE) | cylinder |
| | distance (mm) | 170 |
| | SE length (mm) | 250 |
| | CE length (mm) | 500 |
| | speed SE/min | 5 |
| voltage | SE (kV) | 60 |
| | CE (kV) | −5 | temperature 22° C., humidity 45%

EXAMPLE 2

Totally Biodegradable Layers of Nanofibres with Incorporated Caffeine

For the production of totally biodegradable double layers, combinations of polylactic acid and polycaprolactone were proposed, viz. PLA with caffeine+PLA, PCL with caffeine+PCL, PLA with caffeine+PCL and PCL with caffeine+PLA. The double layer PCL. with caffeine+PCL was prepared using an NS LAB 500 device from the solution AA:FA 2:1 consisting of 12% of polymer, possibly also the model substance caffeine. All other layers were produced on an EMW prototype 1600; PCL from the same solution as that on the LAB and PLA from CHCl3:DCE:EtAc 61:29:10 as a 7% solution, with an addition of 1 g of TEAB to 100 g of solution. The layers with caffeine contained always 5 weight percent of this model substance for polymer dry mass.

Detailed conditions for spinning are shown in the following table.

| PLA and PLA with caffeine, EMW 1600 prototype | | |
|---|---|---|
| electrodes | spinning (SE) | wire (3x) |
| | collecting (CE) | wire (3x) |
| | distance (mm) | 180 |
| | SE length (mm) | 1000 |
| | CE length (mm) | 1000 |
| voltage | SE (kV) | 60 |
| | CE (kV) | −20 | temperature 22° C., humidity 29%

| PCL and PCL with caffeine, EMW 1600 prototype | | |
|---|---|---|
| electrodes | spinning (SE) | wire (3x) |
| | collecting (CE) | wire (3x) |
| | distance (mm) | 180 |
| | SE length (mm) | 1000 |
| | CE length (mm) | 1000 |
| voltage | SE (kV) | 60 |
| | CE (kV) | −20 | temperature 21° C., humidity 30%

| PCL and PCL with caffeine on NS LAB 500 | | |
|---|---|---|
| electrodes | spinning (SE) | 5-wire |
| | collecting (CE) | cylinder |
| | distance (mm) | 170 |
| | SE length (mm) | 200 |
| | CE length (mm) | 500 |
| | speed SE/min | 5 |
| voltage | SE (kV) | 70 |
| | CE (kV) | — | temperature 22° C., humidity 26%

Figure 5:
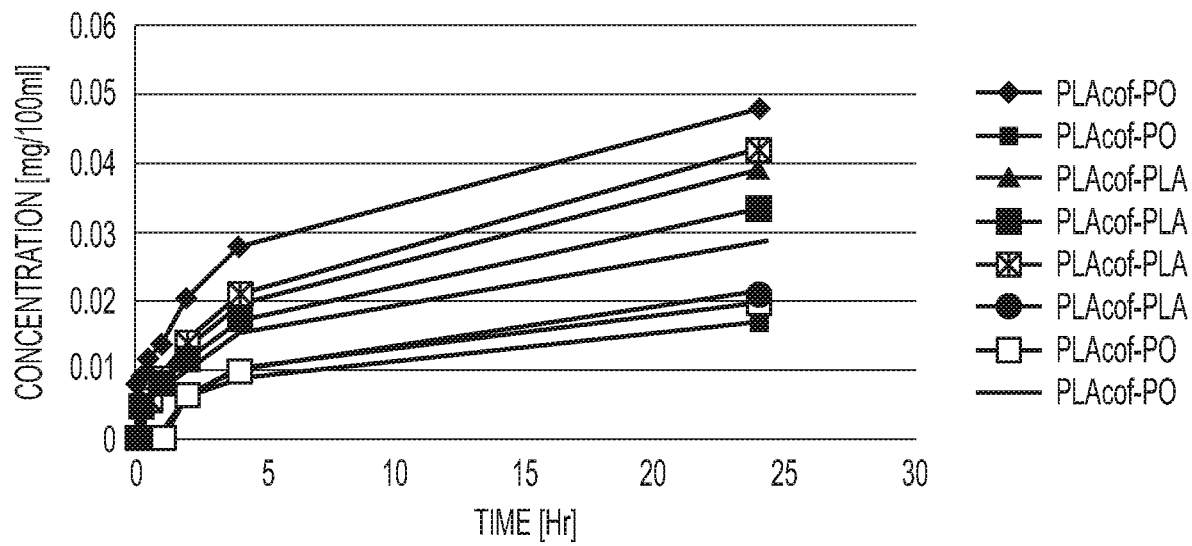
FIG. 5 depicts long-term liberation profiles from nanofibres of polylactic acid with 5% of caffeine and with various layering.
Figure 6A:
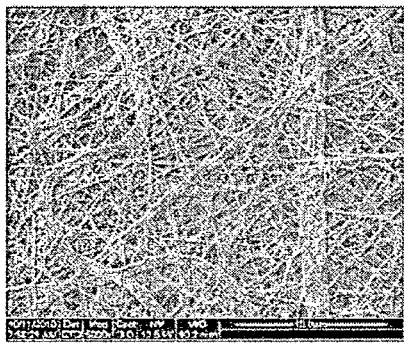
FIG. 6A depicts layers of nanofibres from PCL polymers containing paracetamol in 5000× magnification.
Figure 6B:
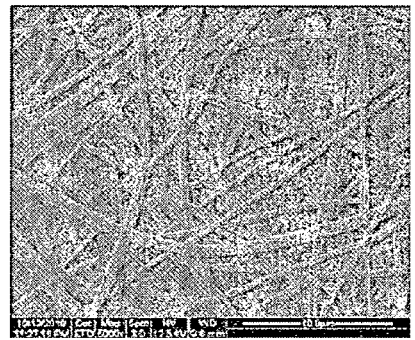
FIG. 6B depicts layers of nanofibres from PLA polymers containing paracetamol in 5000× magnification.
Figure 6C:
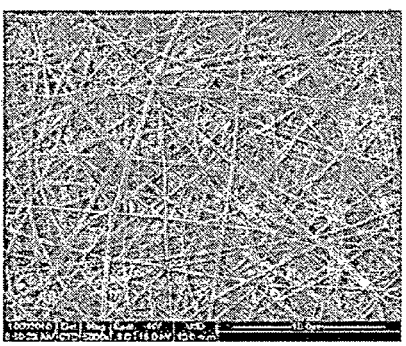
FIG. 6C depicts layers of nanofibres from PVA polymers containing paracetamol in 5000× magnification.
Figure 6D:
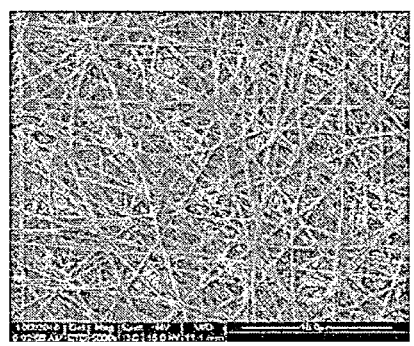
FIG. 6D depicts layers of nanofibres from PAA polymers containing paracetamol in 5000× magnification.
Figure 6E:
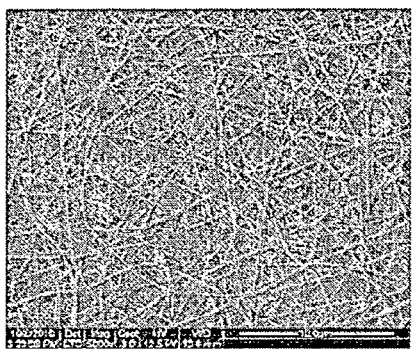
FIG. 6E depicts layers of nanofibres from chitosan, cross-linked polymers containing paracetamol in 5000× magnification.
Figure 6F:
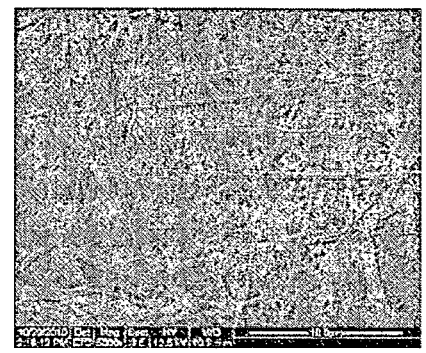
FIG. 6F depicts layers of nanofibres from gelatine, cross-linked polymers containing paracetamol in 5000× magnification.

Long-term liberation profiles from nanofibres of polylactic acid with 5% of caffeine and various layering are represented in FIG. 5.

EXAMPLE 3

Nanofibrous Layers with Paracetamol

During the incorporation of paracetamol (N-acetyl-p-aminophenol) into nanofibres, the crushed commercially available preparation PARALEN® 500 was added into the polymer solution before spinning. The preparation is very well soluble in water, which makes its administration in combination with biopolymers spun mostly from aqueous solutions more advantageous. In solvent mixtures containing water, paracetamol produced ideal solutions. Spinning of specified biopolymers was performed using an NS LAB 500 device, spinning of PLA on an EMW prototype 1600.

FIG. 6 shows the produced layers, in the case of necessity already cross-linked. Verification of paracetamol content was done only for orientation purposes according to the surface weight, which in the samples with paracetamol was naturally' higher than in the clean layers without the drug. The following table gives a list of solutions subjected to spinning, including the paracetamol content for dry mass, and simultaneously the conditions of individual processes.

The essay resulted in the production of very neat fibres having a transverse diameter of 80-600 nm, only in the case of gelatine there occurred some thickened fibres, in PCL besides the thickened fibres the balls of the polymer were also present.

| 12% PCL AA:FA 2:1 + 5% paracetamol for dry mass | | |
|---|---|---|
| electrodes | spinning (SE) | 5-wire |
| | collecting (CE) | cylinder |
| | distance (mm) | 180 |
| | SE length (mm) | 200 |
| | CE length (mm) | 500 |
| | speed SE/min | 5 |
| voltage | SE (kV) | 75 |
| | CE (kV) | — | temperature 20.5° C., humidity 30%

| 11% (PVA + PEO) in H$_2$O + 5% paracetamol for dry mass | | |
|---|---|---|
| electrodes | spinning (SE) | cylinder |
| | collecting (CE) | cylinder |
| | distance (mm) | 125 |
| | SE length (mm) | 200 |
| | CE length (mm) | 500 |
| | speed SE/min | 2.5 |
| voltage | SE (kV) | 55 |
| | CE (kV) | — | temperature 22° C., humidity 29%
Cross-linking 145° C., 15 min

| 2.25% chitosan AA:H$_2$O 2:1 + 10% paracetamol for dry mass | | |
|---|---|---|
| electrodes | spinning (SE) | 5-wire |
| | collecting (CE) | cylinder |
| | distance (mm) | 190-175 |
| | SE length (mm) | 200 |
| | CE length (mm) | 500 |
| | speed SE/min | 3 |
| voltage | SE (kV) | 80-82 |
| | CE (kV) | — | temperature 22° C., humidity 28%
cross-linking 130° C., 10 min

| 7% PLA CHCl$_3$:DCE:EtAc 61:29:10 + 5% paracetamol for dry mass | | |
|---|---|---|
| electrodes | spinning (SE) | wire (3x) |
| | collecting (CE) | wire (3x) |
| | distance (mm) | 180 |
| | SE length (mm) | 1000 |
| | CE length (mm) | 1000 |
| | speed SE/min | — |
| voltage | SE (kV) | 60 |
| | CE (kV) | −20 | temperature 21° C., humidity 33%

| 5% PAA in 0.1M NaCl + beta-cyclodextrin 20% + paracetamol 5% | | |
|---|---|---|
| electrodes | spinning (SE) | cylinder |
| | collecting (CE) | cylinder |
| | distance (mm) | 180 |
| | SE length (mm) | 200 |
| | CE length (mm) | 500 |
| | speed SE/min | 2 |
| voltage | SE (kV) | 35-40 |
| | CE (kV) | — | temperature 24.5° C., humidity 31-32%
Cross-linking 145° C., 12 min

| 11% gelatine AA:H$_2$O 4:1 + 5% paracetamol for dry mass | | |
|---|---|---|
| electrodes | spinning (SE) | cylinder |
| | collecting (CE) | cylinder |
| | distance (mm) | 150 |
| | SE length (mm) | 200 |
| | CE length (mm) | 500 |
| | speed SE/min | 2 |
| voltage | SE (kV) | 70 |
| | CE (kV) | — | temperature 21° C., humidity 29%
cross-linking: vapours of 25% glutaraldehyde, 1-2 h

EXAMPLE 4

Nanofibrous Layers with Nabumetone

Nabumetone, (4-(6-methoxy-2-nafthyl)-2-butanon), belongs to the group of non-steroidal anti-inflammatory drugs (NSAID) and is used to cure inflammations and pains e.g. in arthritis. This derivative of 1-naphthaleneacetic acid is very well soluble in water and can be incorporated with advantage into the polymers spun from aqueous solutions. For experiments with nabumetone, an addition of this drug into polyvinyl alcohol and polyacrylic acid was proposed.

| 11% (PVA + PEO) in H$_2$O + 5% nabumetone for dry mass | | |
|---|---|---|
| electrodes | spinning (SE) | cylinder |
| | collecting (CE) | cylinder |
| | distance (mm) | 130 |
| | SE length (mm) | 200 |
| | CE length (mm) | 500 |
| | speed SE/min | 2.5 |
| voltage | SE (kV) | 60 |
| | CE (kV) | — | temperature 22° C., humidity 30%
cross-linking 145° C., 15 min

| 2.25% chitosan AA:H$_2$O 2:1 overlayering | | |
|---|---|---|
| electrodes | spinning (SE) | cylinder |
| | collecting (CE) | cylinder |
| | distance (mm) | 160 |
| | SE length (mm) | 200 |
| | CE length (mm) | 500 |
| | speed SE/min | 3 |
| voltage | SE (kV) | 82 |
| | CE (kV) | — | temperature 22° C., humidity 29.5%

| 5% PAA in 0.1M NaCl + beta-cyclodextrin 20%, overlayering | | |
|---|---|---|
| electrodes | spinning (SE) | cylinder |
| | collecting (CE) | cylinder |
| | distance (mm) | 170 |
| | SE length (mm) | 200 |
| | CE length (mm) | 500 |
| | speed SE/min | 3 |
| voltage | SE (kV) | 60-65 |
| | CE (kV) | — | cross-linking 20 min at 145° C.

Double layers were produced consisting of a biodegradable layer with a drug overlayered with a biodegradable polymer, i.e. PVA with nabumetone overlayered with pure PVA, chitosan or polyacrylic acid.

To both biopolymers always 5% of nabumetone for dry mass was added, already into the solution before spinning.

The spinning itself was performed on a NS LAB 500 device under the conditions shown in the table below. Due to the spinning of PVA as well as PAA from aqueous solution, it was necessary to perform cross-linking of the samples before dispatch.

Figure 7A:
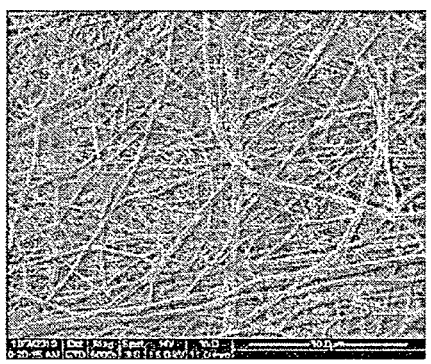
FIG. 7A depicts layers of nanofibres from PVA with nabumetone, not overlayered and not cross-linked in 5000× magnification.
Figure 7B:
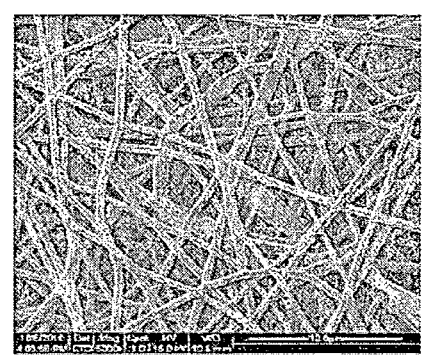
FIG. 7B depicts layers of nanofibres from PVA with nabumetone overlayered with PAA, not cross-linked in 5000× magnification.

FIGS. 7a, 7b show the pictures of samples before cross-linking.

Figure 8:
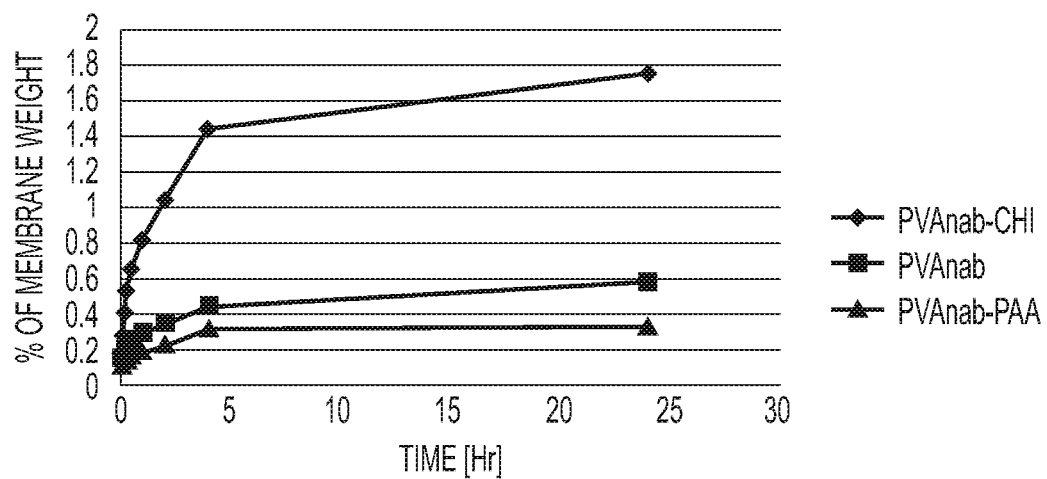
FIG. 8 depicts courses of liberation of nabumetone from polymer layers.
Figure 9A:
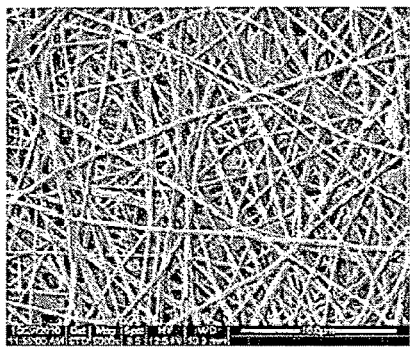
FIG. 9A depicts layers of nanofibres containing PVA with sumatriptane in a quantity of 5% for the dry mass of the polymer in 5000× magnification.
Figure 9B:
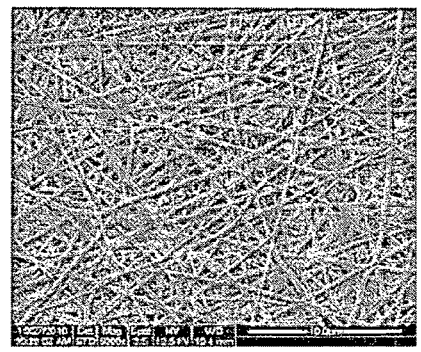
FIG. 9B depicts layers of nanofibres containing PVA with sumatriptane in a quantity of 5% for the dry mass overlayered with PVA in 5000× magnification.
Figure 9C:
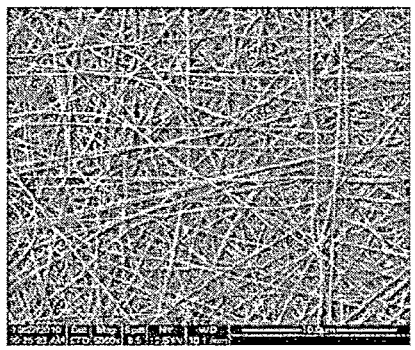
FIG. 9C depicts layers of nanofibres containing PVA with sumatriptane in a quantity of 5% for the dry mass overlayered with chitosan in 5000× magnification.
Figure 9D:
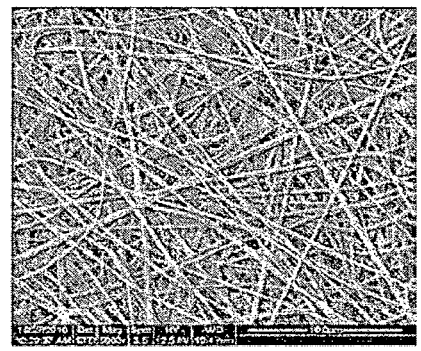
FIG. 9D depicts layers of nanofibres containing PVA with sumatriptane in a quantity of 5% for the dry mass overlayered with PAA in 5000× magnification.

The courses of liberation of nabumetone from polymer layers produced through electrostatic spinning of PVA, combination of PVA with chitosan (CHI) and combination of PVA with PAA are shown in FIG. 8.

EXAMPLE 5

Nanofibrous Layers with Sumatriptane

Sumatriptane, (1-[3-(2-dimethylaminoethyl)-1H-indol-5-yl]-N-methyl-methanesulfonamide), belongs to the drugs with an antimigranious effect used to cure a headache. Due to its good solubility in water this drug was selected to be incorporated into biopolymers spun mostly from water.

Totally biodegradable double layers combining PVA, PAA and chitosan were produced. Namely the drug was incorporated into the fibres of polyvinyl alcohol and subsequently overlayered with pure PVA, chitosan or polyacrylic acid.

In the solution itself prior to spinning and after, pH, the decisive parameter for the occurrence of sumatriptane in its ionised or non-ionised form, was monitored. For the whole time the value of pH varied in the range of 2-3, i.e. in a strong acidic range. All samples were cross-linked under the conditions of cross-linking of PVA (145° C., 20 min), though for chitosah a shorter period of time and a lower temperature would be sufficient.

Figure 10:
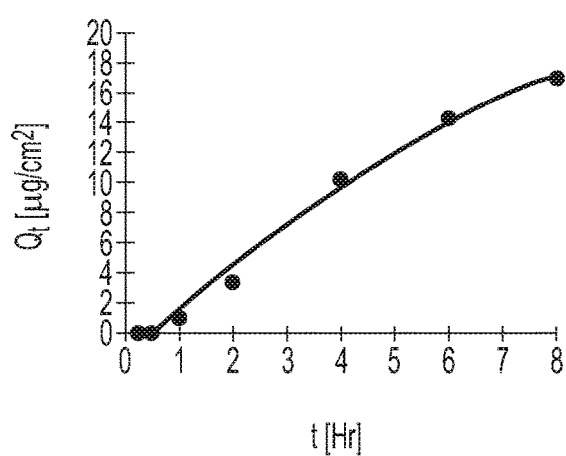
FIG. 10 graphically represents in vitro penetration of sumatriptane from a nanofibrous PVA carrier through the sublingual mucosa.

The following table submits a detailed survey of the conditions of the production process of layers and membranes. The photos of the produced cross-linked samples from an electron microscope in 5000× magnification are shown in FIG. 9 and in vitro penetration of sumatriptane through the sublingual mucosa of nanofibrous PVA carrier is presented in FIG. 10.

| | 11% (PVA + PEO) in H$_2$O + sumatriptane 5% for dry mass | |
|---|---|---|
| electrodes | spinning (SE) | cylinder |
| | collecting (CE) | cylinder |
| | distance (mm) | 130 |
| | SE length (mm) | 200 |
| | CE length (mm) | 500 |
| | speed SE/min | 2.5 |
| voltage | SE (kV) | 60 |
| | CE (kV) | — |
| | 2.25% chitosan AA:H$_2$O 2:1 overlayering | |
| electrodes | spinning (SE) | cylinder |
| | collecting (CE) | cylinder |
| | distance (mm) | 160 |
| | SE length (mm) | 200 |
| | CE length (mm) | 500 |
| | speed SE/min | 3 |
| voltage | SE (kV) | 82 |
| | CE (kV) | — |
| temperature 22° C., humidity 29.5% | | |
| | 11% (PVA + PEO) in H$_2$O overlayering | |
| electrodes | spinning (SE) | cylinder |
| | collecting (CE) | cylinder |
| | distance (mm) | 130 |
| | SE length (mm) | 200 |
| | CE length (mm) | 500 |
| | speed SE/min | 2.5 |
| voltage | SE (kV) | 60 |
| | CE (kV) | — |
| | 5% PAA in 0.1M NaCl + beta-cyclodextrin 20%, overlayering | |
| electrodes | spinning (SE) | cylinder |
| | collecting (CE) | cylinder |
| | distance (mm) | 170 |
| | SE length (mm) | 200 |
| | CE length (mm) | 500 |
| | speed SE/min | 3 |
| voltage | SE (kV) | 60-65 |
| | CE (kV) | — | cross-linking 20 min at 145° C.

APPLICABILITY IN INDUSTRY

The carrier according to the invention has been designed for oromucosal, especially sublingual administration of physiologically active substances, especially of medicinal drugs. Sublingual administration of drugs and/or other physiologically active substances, when compared with oral administration, makes it possible to substantially reduce the total dose of a drug and/or other physiologically active substance administered into the organism, which reduces toxicological loading of the organism, and in the case of expensive medicaments it also decreases the cost of therapy. In comparison with injection administration, the administration is painless and in comparison with inhalation administration it features higher reproducibility.

The invention claimed is:

1. A method for preparing nanofibers by electrospinning, which nanofibers comprise a mixture of polymers, including a polymer suitable as an adhesive to a wall of a mouth cavity and a drug and/or other physiologically active substance, the method comprising:
   (i) dissolving or suspending the polymer suitable as an adhesive to a wall of a mouth cavity in a solvent to obtain a solution;
   (ii) dissolving or suspending the drug or other physiologically active substance in the solution to obtain a mixture; and
   (iii) electrostatic spinning the mixture to obtain two or more layers of nanofibers;
   wherein the two or more layers of nanofibers comprise a nanofiber layer characterized by at least a portion of the polymer suitable as an adhesive to a wall of a mouth cavity attached to a polymer layer comprising the drug or other physiologically active substance.

2. The method of claim 1, further comprising dissolving or suspending a polymer suitable as a covering layer in a solvent to obtain a second solution; and electrostatic spinning the second solution to obtain the covering layer, wherein the two or more layers of nanofibers are positioned on the covering layer after electrostatic spinning the mixture and electrostatic spinning the second solution.

3. The method of claim 2, wherein the polymer suitable as a covering layer comprises polycaprolactone.

4. The method of claim 2, wherein the two or more layers of nanofibers comprise the drug or other physiologically active substance evenly distributed across the two or more layers.

5. A method of producing a carrier for oromucosal administration of physiologically active substances to a subject, comprising:
   (i) dissolving or suspending a first polymer suitable for forming a physiologically acceptable nanofiber in a solvent to obtain a solution;
   (ii) dissolving or suspending a drug or other physiologically active substance in the solution to obtain a mixture;
   (iii) electrostatic spinning the mixture to obtain a flexible layer of nanofibers comprising the drug or other physiologically active substance; and
   (iv) dividing the flexible layer of nanofibres into a plurality of portions based on a predetermined specified size or a predetermined weight,
   wherein the flexible layer of nanofibers comprises the drug or other physiologically active substance evenly distributed across the flexible layer.

6. The method of claim 5, further comprising dissolving or suspending a second polymer suitable as a covering layer in a solvent to obtain a second solution; and electrostatic spinning the second solution to obtain the covering layer, wherein the flexible layer of nanofibers is positioned on the covering layer after electrostatic spinning the mixture and electrostatic spinning the second solution.

7. The method of claim 6, further comprising:
   (i) dissolving or suspending a third polymer suitable for forming a physiologically acceptable nanofiber in a third solvent to obtain a third solution;
   (ii) dissolving or suspending a second drug or other physiologically active substance in the third solution to obtain a third mixture;
   (iii) electrostatic spinning the third mixture to obtain a second flexible layer of nanofibers comprising the second drug or other physiologically active substance.

8. The method of claim 7, wherein the first polymer and the third polymer comprise different polymers, wherein when subject to electrostatic spinning, nanofibers comprising the first polymer and nanofibers comprising the third polymer each have a different rate of release of the first drug or other physiologically active substance and the second drug or other physiologically active substance in a mouth cavity of a subject.

9. The method of claim 5, wherein the drug or other physiologically active substance comprises two or more different drugs or physiologically active substances.

10. The method of claim 9, wherein the method further comprises:
    (i) dissolving or suspending a second polymer suitable for forming a physiologically acceptable nanofiber in a second solvent to obtain a second solution;
    (ii) dissolving or suspending a second drug or other physiologically active substance in the second solution to obtain a second mixture; and
    (iii) electrostatic spinning the second mixture to obtain a second flexible layer of nanofibers comprising the second drug or other physiologically active substance,
    wherein the second flexible layer of nanofibers comprises the second drug or other physiologically active substance evenly distributed across the second flexible layer.

11. The method of claim 10, wherein the second mixture is combined with the first mixture prior to electrostatic spinning.

12. The method of claim 5, wherein the flexible layer of nanofibers is composed of nanofibers having a transverse diameter range between 80-600 nm.

13. The method of claim 5, wherein the electrostatic spinning comprises an electrical field created between a spinning electrode and a collecting electrode to produce the flexible layer of nanofibers comprising the drug or other physiologically active substance evenly distributed across the flexible layer.

14. The method of claim 5, wherein the process further comprises coating or sinking the flexible layer of nanofibers, or one of more of the plurality of portions, in a solution comprising the drug and/or other physiologically active substance.

* * * * *